(12) United States Patent
Johansson et al.

(10) Patent No.: US 12,148,513 B2
(45) Date of Patent: Nov. 19, 2024

(54) MEDICAL INDICATION DETERMINATION USING NEURAL NETWORK PREDICTION ENGINE

(71) Applicant: Change Healthcare Holdings LLC, Nashville, TN (US)

(72) Inventors: Henrik Johansson, El Cerrito, CA (US); Tom Conti, Monona, WI (US); Tate Campbell, Richmond, CA (US); Bardia Afshin, Walnut Creek, CA (US); Justin Schield, Madison, WI (US); Daniel Anderson, Madison, WI (US); Jared Lindaman, Rockton, IL (US)

(73) Assignee: CHANGE HEALTHCARE HOLDINGS LLC, Nashville, TN (US)

( * ) Notice: Subject to any disclaimer, the term of this patent is extended or adjusted under 35 U.S.C. 154(b) by 692 days.

(21) Appl. No.: 16/836,575

(22) Filed: Mar. 31, 2020

(65) Prior Publication Data
US 2021/0304857 A1 Sep. 30, 2021

(51) Int. Cl.
| | |
|---|---|
| G16H 10/60 | (2018.01) |
| G06F 40/30 | (2020.01) |
| G06N 3/08 | (2023.01) |
| G16H 40/63 | (2018.01) |
| G16H 40/67 | (2018.01) |
| G16H 50/30 | (2018.01) |

(52) U.S. Cl.
CPC ............ *G16H 10/60* (2018.01); *G06F 40/30* (2020.01); *G06N 3/08* (2013.01); *G16H 40/63* (2018.01); *G16H 40/67* (2018.01); *G16H 50/30* (2018.01)

(58) Field of Classification Search
CPC ........ G16H 10/60; G16H 40/67; G16H 50/30; G16H 40/63; G06F 40/30; G06N 3/08
USPC ...................................................... 705/2–3
See application file for complete search history.

(56) References Cited

U.S. PATENT DOCUMENTS

| | | | |
|---|---|---|---|
| 2003/0204415 A1* | 10/2003 | Knowlton | G16H 20/10 600/300 |
| 2010/0106523 A1* | 4/2010 | Kalamas | G16H 70/40 705/3 |
| 2011/0161114 A1* | 6/2011 | Kalamas | G16H 10/60 705/2 |
| 2012/0203574 A1* | 8/2012 | Kalamas | G16H 70/40 705/3 |
| 2014/0278475 A1* | 9/2014 | Tran | G16H 20/30 705/2 |
| 2017/0286830 A1* | 10/2017 | El-Yaniv | G06N 3/045 |
| 2019/0214145 A1* | 7/2019 | Kurek | A61K 31/366 |
| 2020/0388360 A1* | 12/2020 | Caffarel | G06N 3/04 |
| 2021/0134431 A1* | 5/2021 | Garcia | G16H 10/60 |

* cited by examiner

*Primary Examiner* — Michael Tomaszewski
(74) *Attorney, Agent, or Firm* — Myers Bigel, P.A.

(57) ABSTRACT

A method includes receiving first information associated with a patient, second information associated with a provider, and third information associated with an order, and determining, using a multi-layer neural network, a medical indication corresponding to the order responsive to receiving the first information, the second information, and the third information.

20 Claims, 9 Drawing Sheets

MEDICAL INDICATION DETERMINATION USING NEURAL NETWORK PREDICTION ENGINE

FIELD

The present inventive concepts relate generally to health care systems and services and, more particularly, medical indication selection by a health care provider as a basis for performing and/or prescribing a test, procedure, surgery, and/or medication.

BACKGROUND

As part of a workflow for administering care to patients, health care service providers place orders through Electronic Medical Records (EMR)/order entry systems. An order may be, for example, instructions to perform a test or procedure and/or may be a prescription for a medication or medical device. In addition to entering the order, a health care service provider may also be required to provide a medical indication for the order. A medical indication may be viewed as a reason to issue an order, e.g., a criterion for when it is appropriate to perform a particular test, prescribe a particular medication, etc. There are thousands of medical indications for health care service providers to choose from when placing an order. These medical indications may also be associated with Appropriate Use Criteria (AUC), which are developed by various medical specialty societies. Government regulations, such as those associated with Medicare, for example, may require health care service providers ordering particular exams for Medicare patients to consult AUC through a qualified decision support mechanism. This may require a health care service provider to search through a large number of possible indications as the qualified decision support mechanisms typically generate a lengthy list of proposed indications based on a patient's age and gender along with the order. Additional information associated with a patient's medical record and care may not be considered by these decision support mechanisms.

SUMMARY

According to some embodiments of the inventive concept, a method comprises receiving first information associated with a patient, second information associated with a provider, and third information associated with an order; and determining, using an artificial intelligence engine, a medical indication corresponding to the order responsive to receiving the first information, the second information, and the third information.

In other embodiments, the artificial intelligence engine comprises a multi-layer neural network and a content similarity engine. The medical indication is a first medical indication. The method further comprises receiving a free-text reason for the order; and determining, using the content similarity engine, a second medical indication corresponding to the order responsive to receiving the free-text reason.

In still other embodiments, determining, using the artificial intelligence engine, the first medical indication comprises determining, using the multi-layer neural network, a first plurality of medical indications corresponding to the order responsive to the first information, the second information, and the third information. Determining, using the content similarity engine, the second medical indication comprises determining using the content similarity engine, a second plurality of medical indications responsive to the free-text reason.

In still other embodiments, the first plurality of medical indications have a first plurality of scores associated therewith, respectively and the second plurality of medical indications have a second plurality of scores associated therewith, respectively. The method further comprises generating a third plurality of medical indications, the third plurality of medical indications comprising a combination of the first plurality of medical indications and the second plurality of medical indications, each of the third plurality of medical indications having a respective one of the first plurality of scores associated therewith and a respective one of the second plurality of scores associated therewith, such that the respective one of the first plurality of scores is zero when the respective one of the third plurality of medical indications is not in the first plurality of medical indications and the respective one of the second plurality of scores is zero when the respective one of the third plurality of medical indications is not in the second plurality of medical indications; and generating a third plurality of scores associated with the third plurality of medical indications, respectively. The third plurality of scores comprises a plurality of weighted averages of the first plurality of scores associated with the third plurality of medical indications and the second plurality of scores associated with the third plurality of medical indications, respectively.

In still other embodiments, the third plurality of scores corresponds to probabilities of the third plurality of medical indications being applicable to the order, respectively. The method further comprises communicating to an order entry system for entry therein, without input from the provider, an automatic selection of one of the third plurality of medical indications having a highest one of the probabilities associated therewith when the highest one of the probabilities exceeds a threshold.

In still other embodiments, the method further comprises communicating to the order entry system N of the third plurality of medical indications having N highest probabilities associated therewith, respectively, when the highest one of the probabilities does not exceed the threshold, where N is less than a total number of the plurality of third medical indications.

In still other embodiments, the threshold is a first threshold. The method further comprises communicating to the order system an indication that none of the third plurality of medical indications is applicable to the order when a highest one of the probabilities is less than a second threshold.

In still other embodiments, the method further comprises receiving an encounter diagnosis for the patient and a body area identification of the order; combining the encounter diagnosis for the patient, the body area identification of the order, and the free-text reason for the order to generate a clinical input text; numerically encoding the clinical input text into a first sequence of words to create a clinical input vocabulary, the first sequence of words having first weights associated therewith, respectively, that are each indicative of the importance of respective ones of the first sequence of words in the clinical input vocabulary; numerically encoding a plurality of possible medical indications into a second sequence of words to create a possible medical indications vocabulary, the second sequence of words having second weights associated therewith, respectively, that are each indicative of the importance of respective ones of the second sequence of words in the possible medical indications vocabulary; embedding the numerically encoded clinical input text into a clinical input vector; embedding the numerically encoded plurality of possible medical indications into a plurality of possible medical indications vectors; and determining a dot-product of the clinical input vector with each of the plurality of possible medical indications vectors. Determining, using the content similarity engine, the second medical indication responsive to receiving the free-text reason comprises determining the second medical indication based on the dot-product of the clinical input vector with each of the plurality of possible medical indications vectors.

In still other embodiments, the method further comprises duplicating a first phrase in each of the plurality of possible medical indications before numerically encoding the plurality of possible medical indications into the second sequence.

In still other embodiments, the first information associated with the patient comprises an age, a gender, a problem list, an encounter diagnosis, a patient class, and/or a medical center department; the second information associated with the provider comprises a provider identifier and/or a provider specialty; and the third information associated with the order comprises an order name, order identification, order modality, order contrast, and/or body area identification.

In still other embodiments, the method further comprises organizing the first, second, and third information into numeric value information, categorical value information, and sequence of categorical values information; scaling the numerical value information to a defined range to generate scaled numerical value information; numerically encoding the categorical value information to create a categorical value information vocabulary; numerically encoding the sequence of categorical values information to create a sequence of categorical values vocabulary; embedding, using a first layer of the neural network, the numerically encoded categorical value information into a categorical value information input vector; and embedding, using the first layer of the neural network, the numerically encoded sequence of categorical values information into a sequence of categorical values information input vector.

In still other embodiments, the method further comprises concatenating, using a second layer of the neural network, the scaled numerical value information, the categorical value information input vector, and the sequence of categorical values information input vector. Determining, using a multi-layer neural network, the medical indication comprises determining, using a third layer of the neural network, the medical indication corresponding to the order responsive to a concatenation of the scaled numerical value information, the categorical value information input vector, and the sequence of categorical values information input vector.

In still other embodiments, the first and second layers of the multi-layer neural network are configured to automatically perform feature extraction on the numeric value information, the categorical value information, the sequence of categorical values information, or the text information to reduce the dimensionality thereof.

In still other embodiments, the third layer of the multi-layer neural network is a classification layer that is configured to perform supervised learning of correlations between the scaled numerical value information, the categorical value information input vector, the sequence of categorical values information input vector, and the text information input vector and a plurality of possible medical indications based on the feature extraction performed by the second layer of the multi-layer neural network.

According to some embodiments of the inventive concept, a method comprises: receiving first information associated with a patient, second information associated with a provider, and third information associated with an order; generating an input data set for a multi-layer neural network based on the first information, the second information, and the third information; using a featurization layer of the multi-layer neural network to automatically perform feature extraction on the input data set to reduce the dimensionality thereof; and using a classification layer of the multi-layer neural network to perform supervised learning of correlations between the input data set and a plurality of possible medical indications based on the feature extraction performed on the input data set.

In further embodiments, generating the input data set comprises: defining a contiguous range for a first portion of the input data set; defining a maximum sequence length of a second portion of the input data set; assigning weights to words corresponding to a third portion of the input data set; or scaling a fourth portion of the input data set to a defined range.

In still further embodiments, the featurization layer comprises a first featurization layer and a second featurization layer. The method further comprises: using the first featurization layer of the multi-layer neural network to embed a first portion of the input data set into a plurality of vectors having dimensions that are representative of the first portion of the input data set; and using the second featurization layer of the multi-layer neural network to concatenate the plurality of vectors and numerical data of the input data set.

In still further embodiments, using the classification layer of the multi-layer neural network to perform supervised learning of correlations between the input data set and the plurality of possible medical indications comprises using the classification layer of the multi-layer neural network to perform supervised learning of correlations between the input data set and the plurality of possible medical indications responsive to a concatenation of the plurality of vectors and numerical data of the input data set.

In still further embodiments, the first information associated with the patient comprises an age, a gender, a problem list, an encounter diagnosis, a patient class, and/or a medical center department; the second information associated with the provider comprises a provider identifier and/or a provider specialty; and the third information associated with the order comprises an order name, order identification, order modality, order contrast, and/or body area identification.

In still further embodiments, the method further comprises receiving a free-text reason for the order; and applying natural language processing to the free-text reason to determine correlations between the free-text reason and the plurality of possible medical indications.

In some embodiments of the inventive concept, a system comprises a processor; and a memory coupled to the processor and comprising computer readable program code embodied in the memory that is executable by the processor to perform operations comprising: receiving first information associated with a patient, second information associated with a provider, and third information associated with an order; and determining, using an artificial intelligence engine, a medical indication corresponding to the order responsive to receiving the first information, the second information, and the third information.

In some embodiments of the inventive concept, a system comprises a processor; and a memory coupled to the processor and comprising computer readable program code embodied in the memory that is executable by the processor to perform comprising: receiving first information associated with a patient, second information associated with a provider, and third information associated with an order;

generating an input data set for a multi-layer neural network based on the first information, the second information, and the third information; using a featurization layer of the multi-layer neural network to automatically perform feature extraction on the input data set to reduce the dimensionality thereof; and using a classification layer of the multi-layer neural network to perform supervised learning of correlations between the input data set and a plurality of possible medical indications based on the feature extraction performed on the input data set.

In some embodiments of the inventive concept, a computer program product comprises a tangible computer readable storage medium comprising computer readable program code embodied in the medium that is executable by a processor to perform operations comprising: receiving first information associated with a patient, second information associated with a provider, and third information associated with an order; and determining, using an artificial intelligence engine, a medical indication corresponding to the order responsive to receiving the first information, the second information, and the third information.

In some embodiments of the inventive concept, a computer program product comprises a tangible computer readable storage medium comprising computer readable program code embodied in the medium that is executable by a processor to perform operations comprising: receiving first information associated with a patient, second information associated with a provider, and third information associated with an order; generating an input data set for a multi-layer neural network based on the first information, the second information, and the third information; using a featurization layer of the multi-layer neural network to automatically perform feature extraction on the input data set to reduce the dimensionality thereof; and using a classification layer of the multi-layer neural network to perform supervised learning of correlations between the input data set and a plurality of possible medical indications based on the feature extraction performed on the input data set.

It is noted that aspects described with respect to one embodiment may be incorporated in different embodiments although not specifically described relative thereto. That is, all embodiments and/or features of any embodiments can be combined in any way and/or combination. Moreover, other methods, systems, articles of manufacture, and/or computer program products according to embodiments of the inventive concept will be or become apparent to one with skill in the art upon review of the following drawings and detailed description. It is intended that all such additional systems, methods, articles of manufacture, and/or computer program products be included within this description, be within the scope of the present inventive subject matter, and be protected by the accompanying claims. It is further intended that all embodiments disclosed herein can be implemented separately or combined in any way and/or combination.

BRIEF DESCRIPTION OF THE DRAWINGS

Other features of embodiments will be more readily understood from the following detailed description of specific embodiments thereof when read in conjunction with the accompanying drawings, in which.

DETAILED DESCRIPTION

Figure 1:
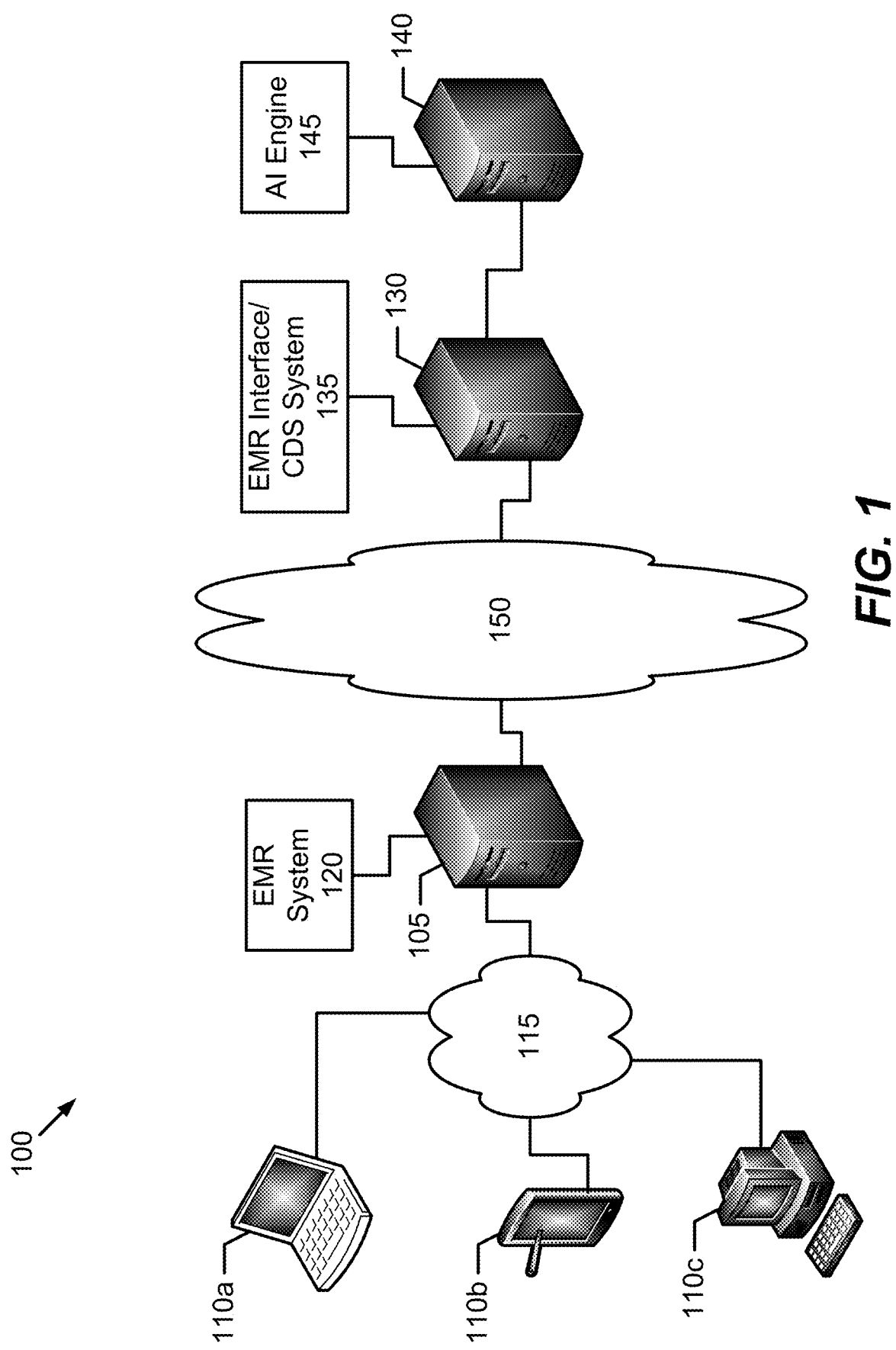
FIG. 1 is a block diagram that illustrates a communication network including an Artificial Intelligence (AI) assisted medical indication selection support system for determining a medical indication for an order in accordance with some embodiments of the inventive concept.

In the following detailed description, numerous specific details are set forth to provide a thorough understanding of embodiments of the present inventive concept. However, it will be understood by those skilled in the art that the present invention may be practiced without these specific details. In some instances, well-known methods, procedures, components and circuits have not been described in detail so as not to obscure the present inventive concept. It is intended that all embodiments disclosed herein can be implemented separately or combined in any way and/or combination. Aspects described with respect to one embodiment may be incorporated in different embodiments although not specifically described relative thereto. That is, all embodiments and/or features of any embodiments can be combined in any way and/or combination.

As used herein, the term "medical indication" refers to a valid reason to order a treatment or procedure, such as, but not limited to, a test, surgery, medication, and medical device. There can be multiple medical indications to order or use a particular treatment or procedure.

Embodiments of the inventive concept are described herein in the context of an artificial intelligence engine comprising a multi-layer neural network and/or a content similarity engine, which includes a natural language processor. It will be understood that other types of artificial intelligence systems can be used in other embodiments of the artificial intelligence engine including, but not limited to, machine learning systems, deep learning systems, and/or computer vision systems. Moreover, it will be understood that the multi-layer neural network described herein is a multi-layer artificial neural network comprising artificial neurons or nodes and does not include a biological neural network comprising real biological neurons.

Some embodiments of the inventive concept stem from a realization that clinical decision support mechanisms and/or medical indication selection algorithms use a limited amount of information associated with a patient, such as age, gender, and an order description, when presenting a health care services provider ("provider") with a list of possible medical indications for an order. This can result in the provider needing to review numerous possible medical indications to select one that best supports a particular order. Some embodiments of the inventive concept may provide an Artificial Intelligence (AI) assisted medical indication selection support system that takes advantage of a variety of different information available that is associated with the patient and/or order to provide a more accurate and focused list of possible medical indications for a given order. For example, in some embodiments, the AI assisted medical indication selection support system may use input information associated with the patient, the provider, and/or the order as a basis for generating one or more possible medical indications corresponding to the order. This patient information may include, but is not limited to, age, gender, problem list, encounter diagnosis, patient class, and/or a medical center department. The provider information may include, but is not limited to, a provider identifier and/or a provider specialty. In accordance with various embodiments of the inventive concept, the scope of recognition for the provider identifier may span a range of possibilities. For example, the provider identifier may be a site-specific (e.g., hospital or medical practice specific), regional, and/or national identifier. The order information may include, but is not limited to, an order name, order identification, order modality, order contrast, body area identification, and/or a free-text reason for the order.

In some embodiments of the inventive concept, the AI engine used to support the medical indication selection process may include two components: a multi-layer neural network and a content similarity engine, which are used to determine one or more medical indications that may be applicable to an order based on evidence-based guidelines provided by, for example, one or more medical specialty societies, medical schools, government regulations, and the like. These guidelines may be used in the training, knowledge base, and/or vocabulary for the neural network and the content similarity engine. The neural network may be used to process the patient, provider, and order information, except for the free-text reason for the order, to generate one or more possible medical indications for an order. These possible medical indications may have scores associated therewith. The score is indicative of the probability that the medical indication is applicable to the order. When a particular medical indication has a probability that exceeds a defined threshold for an order, then the medical indication may be communicated, for example, to an order entry system and/or an electronic medical record (EMR) system for automatic entry therein thereby alleviating the provider of having to select a medical indication for the order. Thus, some embodiments of the inventive concept may provide a medical service provider relief from the task of reviewing hundreds or thousands of possible medical indications for an order as the selection may be completely automated based on the available patient, provider and/or order information.

There may not be a single medical indication, however, having a probability applicability to the order that exceeds the defined threshold for automatic selection. Embodiments of the inventive concept may, however, narrow down the list of possible medical indications for a provider to consider by presenting the provider with a list of medical indications having the N highest probabilities of being applicable to the order based on their scores. The number N may be selected to provide a manageable amount of medical indications for a provider to review and may also be determined based on cut-offs or gaps between the scores associated with possible medical indications. For example, if there is a relatively small gap between the probabilities associated with the top five possible medical indications, but there is a large gap between the fifth highest probability and the sixth highest probability, then N may be set to five to communicate the top five medical indications to the order entry system/EMR system for review and selection by the provider.

In some circumstances, however, the probabilities associated with the highest probable medical indications may be relatively low. This may indicate that the neural network was unable to find a medical indication for an order that satisfies the evidence-based guidelines on which the neural network is trained. In accordance with various embodiments of the inventive concept, various metrics can be used that measure a confidence level for a medical indication prediction. In some embodiments, a highest one of the probabilities associated with the possible indications may be compared with a defined threshold. When the probability is below the defined threshold, then it can be concluded that no medical indication was found for that particular order. In other embodiments, when a sum of the probabilities of the K possible medical indications having the highest probabilities is below a defined threshold, then it can be concluded that no medical indication was found for that particular order. This "no result" outcome can be communicated to the order entry system/EMR system allowing the provider to select a medical indication manually. In some embodiments, these threshold determinations may be made by a clinical decision support system that can communicate with an order entry system/EMR system based on the probabilities generated by the AI engine. In other embodiments, the AI engine may perform the threshold comparisons and communicate the results to the clinical decision support system.

As described above, the AI engine may also include a content similarity engine. When a provider provides a free-text reason for an order, the content similarity engine can be used to perform natural language processing on the free-text reason to compare the free-text reason with descriptive names of medical indications to determine one or more possible indications for the order. Similar to the neural network, the content similarity engine may assign scores to the possible medical indications that are indicative of the probability that the medical indication is applicable to the order. A combiner may be used to merge the outputs of the neural network with the content similarity engine by weighting the scores associated with the possible medical indications output by neural network and the content similarity engine and computing a weighted average. If a medical indication is in a list of medical indications output by the neural network, but not the content similarity engine, then a weight of zero may be applied to the content similarity engine portion of the weighted average. Similarly, if a medical indication is in a list of medical indications output by the content similarity engine, but not by the neural network, then a weight of zero may be applied to the neural network portion of the weighted average. These weighted average scores may then be used to determine whether to communicate a medical indication to an order entry system/EMR system for automatic entry therein, communicate a list of medical indications having the N highest probabilities to the order system/EMR system, or communicate a "no result" outcome to the order system system/EMR system as described above. The addition of the free-text analysis through the content similarity engine may supplement the neural network to provide improved accuracy in identifying potential medical indications for an order.

Thus, the AI assisted medical indication selection support system, according to some embodiments of the inventive concept, may allow possible medical indications to be identified for an order based on evidence-based guidelines established by accepted authorities. These accepted authorities may include, but are not limited to, recognized or credentialed medical organizations, such as, for example, medical societies associated with various practice specialties, academic institutions, commercial institutions, such as pharmaceutical and/or hospital product companies, governmental organization(s), and/or other applicable entities. Moreover, a provider can save time using the AI assisted medical indication selection support system to automatically select a medical indication for an order that has a high probability of corresponding to the order or by narrowing down a database of numerous possible medical indications to a manageable number of likely possibilities that the provider can quickly review and select from. Some government regulations require that providers use some sort of decision support mechanism when selecting a medical indication and/or an Appropriate Use Criteria (AUC) for an order. The AI assisted medical indication selection support system, according to some embodiments of the inventive concept described herein, may allow providers to comply with governmental regulations requiring the use of some type of clinical decision support mechanism for their orders.

Referring to FIG. 1, a communication network 100 including an AI assisted medical indication selection support system for determining a medical indication for an order, in accordance with some embodiments of the inventive concept, comprises a health care facility server 105 that is coupled to devices 110a, 110b, and 110c via a network 115. The health care facility may be any type of health care or medical facility, such as a hospital, doctor's office, specialty center (e.g., surgical center, orthopedic center, laboratory center etc.), or the like. The health care facility server 105 may be configured with an Electronic Medical Record (EMR) system module 120 to manage patient files and facilitate the entry of orders for patients via health care service providers ("providers"). Although shown as one combined system in FIG. 1, it will be understood that some health care facilities use separate systems for electronic medical record management and order entry management. The providers may use devices, such as devices 110a, 110b, and 110c to manage patients' electronic records and to issue orders for the patients through the EMR system 120. An order may include, but is not limited to, a treatment, a procedure (e.g., surgical procedure, physical therapy procedure, radiologic/imaging procedure, etc.) a test, a prescription, and the like. The network 115 communicatively couples the devices 110a, 110b, and 110c to the health care facility server 105. The network 115 may comprise one or more local or wireless networks to communicate with the health care facility server 105 when the health care facility server 105 is located in or proximate to the health care facility. When the health care facility server 105 is in a remote location from the health care facility, such as part of a cloud computing system or at a central computing center, then the network 115 may include one or more wide area or global networks, such as the Internet.

According to some embodiments of the inventive concept, providers may access an AI assisted medical indication selection support system to assist them in selecting a medical indication for a patient order. The AI assisted medical indication selection support system may include a health care facility interface server 130, which includes an EMR interface/clinical decision support (CDS) system module 135 to facilitate the transfer of information between the EMR system 120, which the providers use to manage patient records and issue orders, and an AI server 140, which includes an AI engine module 145. The AI server 140 and AI engine module 145 may be configured to receive patient information, provider information, and order information contained in records in the EMR system 120 from the health care facility server 105 and EMR system module 120 by way of the health care facility interface server 130 and EMR interface/CDS system module 135. The EMR interface/CDS system module 135 in conjunction with the AI engine module 145 may be further configured to generate a recommendation of one or more possible medical indications for the order when the recommendation can be supported by evidence-based guidelines used by the AI engine module 145. It will be understood that the division of functionality described herein between the AI server/AI engine module 145 and the health care facility interface server 130/EMR interface/CDS system module 135 is an example. Various functionality and capabilities can be moved between the AI server/AI engine module 145 and the health care facility interface server 130/EMR interface/CDS system module 135 in accordance with different embodiments of the inventive concept. Moreover, in some embodiments, the AI server/AI engine module 145 and the health care facility interface server 130/EMR interface/CDS system module 135 may be merged as a single logical and/or physical entity.

A network 150 couples the health care facility server 105 to the health care facility interface server 130. The network 150 may be a global network, such as the Internet or other publicly accessible network. Various elements of the network 150 may be interconnected by a wide area network, a local area network, an Intranet, and/or other private network, which may not be accessible by the general public. Thus, the communication network 150 may represent a combination of public and private networks or a virtual private network (VPN). The network 150 may be a wireless network, a wireline network, or may be a combination of both wireless and wireline networks.

The service provided through the health care facility interface server 130, EMR interface/CDS system module 135, AI server 140 and AI engine module 145 to provide AI assisted medical indication selection support for patient orders may, in some embodiments, be embodied as a cloud service. For example, health care facilities may integrate their EMR systems/order systems with the AI assisted medical indication selection service and access the service as a Web service. In some embodiments, the AI assisted medical indication selection support service may be implemented as a Representational State Transfer Web Service (RESTful Web service).

Although FIG. 1 illustrates an example communication network including an AI assisted medical indication selection support system for determining a medical indication for an order, it will be understood that embodiments of the inventive subject matter are not limited to such configurations, but are intended to encompass any configuration capable of carrying out the operations described herein.

Figure 2:
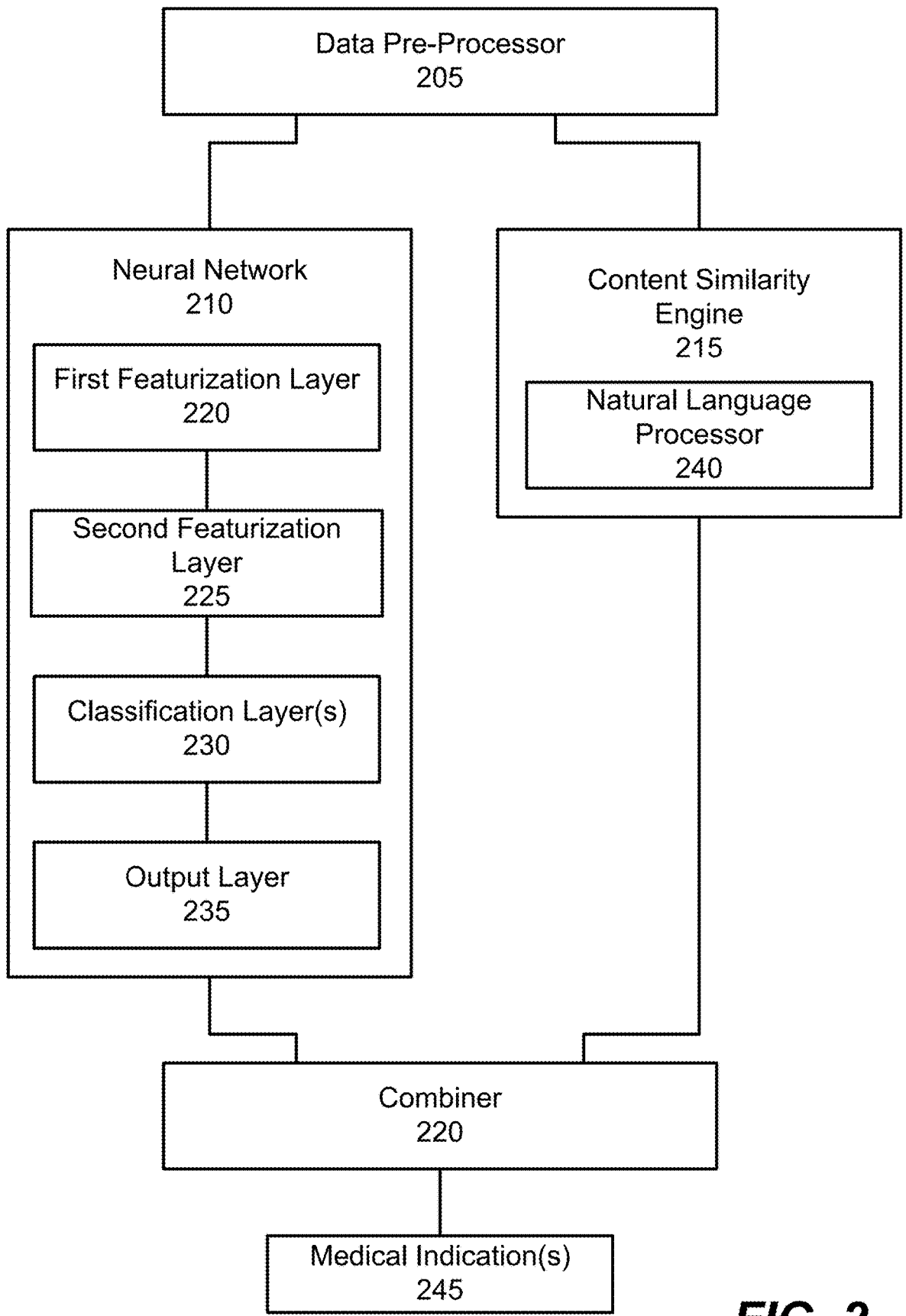
FIG. 2 is a block diagram of an AI engine used in the AI assisted medical indication selection support system of FIG. 1 in accordance with some embodiments of the inventive concept.

FIG. 2 is a block diagram of the AI engine 145 used in the AI assisted medical indication selection support system in accordance with some embodiments of the inventive concept. As shown in FIG. 2, the AI engine 145 may include a data pre-processor module 205, a multi-layer neural network 210, a content similarity engine 215, and a combiner 220 that are connected as shown. The data pre-processor module 205 may be configured to receive information associated with a patient, information associated with a provider, and information associated with an order for the patient from, for example, a health care facility by way of the health care facility interface server 130 and EMR interface/CDS system module 135. The patient information may include, but is not limited to, age, gender, problem list (e.g., description of one or more ailments or conditions the patient is suffering from), encounter diagnosis (the issue that causes a patient to visit the health care provider), patient class (e.g., in-patient or out-patient), and/or a medical center department (e.g., emergency room, cardiology, radiology, etc.). Note that a patient's encounter diagnosis may be different than a patient's problem list. For example, a patient may fall and receive a head injury, which may result in an encounter diagnosis of head trauma. The patient may nevertheless have a problem list description that includes heart disease and arthritis. The provider information may include, but is not limited to, a provider identifier and/or a provider specialty (e.g., cardiology, oncology, etc.). The order information may include, but is not limited to, an order name, order identification, order modality, order contrast, body area identification and/or a free-text reason for the order.

The data pre-processor module 205 may be configured to organize all of this information with the exception of the free-text reason for the order into an input data set for the neural network 210. In some embodiments, the patient, order, and provider information may be organized into numeric value information, categorical value information and sequence of categorical values information. Numerical value information, such as patient age, may be scaled to a defined range, such as a normalization range of 0-1. Categorical values information, such as an order identification number, may be numerically encoded to create a categorical value information vocabulary. That is, the information may be mapped to a number within a contiguous range. Sequence of categorical values information, such as a patient's list of problem codes in a problem list, may be numerically encoded to create a sequence of categorical values information vocabulary, which may define a maximum sequence length.

The data pre-processor module 205 may be further configured to process any free-text reason input that may have been entered by a provider to generate a clinical input text for the content similarity engine 215. In some embodiments, the free-text reason input entered by the provider may be combined with additional information, such as a patient's encounter diagnosis and/or identification of an affected body area, to create the clinical input text that may capture clinical aspects of the reason for an order. The body area information may be obtained from the order that is being placed. For example, a computed tomography (CT) head exam indicates that the affected body area is the patient's head. The data pre-processing module 205 may be further configured to process the list of possible medical indications by duplicating the first phrase in the clinical indication names to place more emphasis on the primary description of the medical indication and lessen the effect of the more granular description of the medical indication.

The neural network 210 may comprise multiple layers including a first featurization layer 220, a second featurization layer 225, one or more classification layer(s) 230, and an output layer 235. The first and second featurization layers 220 and 225 may be configured to automatically perform feature extraction on the input data set from the data pre-processing module 205 to reduce the dimensionality thereof so as to allow the neural network 210 to learn an efficient representation of the input data. According to some embodiments, the first featurization layer may be configured to numerically encode the categorical value information to create a categorical value information vocabulary, to embed the numerically encoded categorical value information into a categorical value information input vector, to numerically encode the sequence of categorical values information to create a sequence of categorical values vocabulary, and to embed the numerically encoded sequence of categorical values information into a sequence of categorical values information input vector. The encoding and embedding processes may comprise representing discrete numbers by a vector of continuous values representing a meaningful aspect of the input data set. The second featurization layer 225 may be configured to concatenate the scaled numerical value information output from the data pre-processor module 205 with the categorical value information input vector, and the sequence of categorical values information input vector. This concatenation may be viewed as a full representation of the input data set. One or more classification layer(s) 230 may be configured to perform supervised learning of correlations between the input data set, as represented by the vector and scaled numerical value information concatenation output from the second featurization layer 225, and a plurality of possible medical indications. A scored list of one or more medical indications for an order input by a provider may be output by the output layer 235. The scores may be indicative of probabilities that the respective medical indication(s) are applicable to the order.

The content similarity engine 215 may be configured to receive the clinical input text and the list of possible medical indications, which may be modified through duplication of the first phrase in the clinical indication names. A natural language processor module 240 may be configured to tokenize both the clinical input text and the possible medical indications into sequences of words to create a clinical input vocabulary and a possible medical indications vocabulary, respectively. As part of this process, spelling errors may be corrected, synonyms may be resolved, and a maximum sequence length may be defined. Words may be weighted by how important they are based on their presence in the individual segment of text as well as in the full data set using, for example, a process called term frequency-inverse document frequency (td-idf) weighting. This may reduce the impact of common words used throughout the data set and may increase the impact of words specific to a segment of text. The natural language processor 240 may generate an encoded and embedded clinical input vector from the clinical input text and may generate a plurality of encoded and embedded possible medical indications vectors. The dot-product of the clinical input vector with each of the plurality of possible medical indications vectors may be used as a measure of similarity of the original free-text reason input with each of the plurality of possible medical indications. If there are no words in common, then the dot-product would be zero. If the match is perfect, then the dot-product would be one. These dot-product values may be used as scores for each of the plurality of possible medical indications with each score representing a probability that the respective medical indication is applicable to the order. In some embodiments the scores may be normalized that the sum of all scores across all possible ones of the possible medical indications is one.

The combiner 220 may receive the scored list of one or more medical indications for an order output by the output layer 235 along with the scored list of possible medical indications output by the content similarity engine 215. The combiner may merge these two lists of medical indications by computing a weighted average for each of the various medical indications. If a medical indication is in the list of medical indications output by the neural network 210, but not the content similarity engine 215, then a weight of zero may be applied to the content similarity engine 215 portion of the weighted average. Similarly, if a medical indication is in a list of medical indications output by the content similarity engine 215, but not by the neural network 210, then a weight of zero may be applied to the neural network portion of the weighted average. These weighted average scores may then be used to determine whether to communicate one or more medical indications 245, to the health care facility server 105 and order entry system/EMR system 120.

The weighted average scores are indicative of the probabilities that respective ones of the medical indications are applicable to an order. Thus, in some embodiments, when a particular medical indication has a weighted average score corresponding to a probability that exceeds a defined threshold for an order, then the medical indication may be communicated, for example, to the health care facility server 105 and order entry system/EMR system 120 for automatic entry therein thereby alleviating the provider of having to select a medical indication for the order.

There may not be a single medical indication, however, having a probability applicability to the order that exceeds the defined threshold for automatic selection. According to some embodiments, the combiner 220 may narrow down the list of possible medical indications for a provider to consider by communicating to the health care facility server 105 and order entry system/EMR system 120 by way of the AI server/AI engine module 145 and the health care facility interface server 130/EMR interface/CDS system module 135 a list of medical indications having the N highest probabilities of being applicable to the order based on their scores. The number N may be selected to provide a manageable amount of medical indications for a provider to review and may also be determined based on cut-offs or gaps between the scores associated with possible medical indications.

The probabilities associated with the highest probable medical indications may, however, be relatively low. This may indicate that the neural network 210 was unable to find a medical indication for an order that satisfies the evidence-based guidelines on which the neural network is trained. Thus, when a highest probability corresponding to one of the possible medical indications is below a defined threshold or, in other embodiments, when a sum of the probabilities of the K possible medical indications having the highest probabilities is below a defined threshold, then it can be concluded that no medical indication was found for that particular order. This "no result" outcome can be communicated to the health care facility server 105 and order entry system/EMR system 120 so as to allow the provider to select a medical indication manually.

Figure 3:
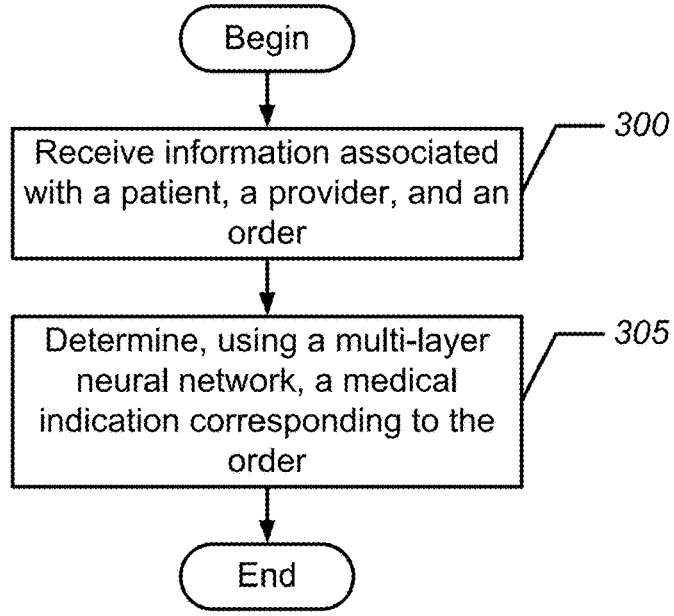
FIGS. 3-9 are flowcharts that illustrate operations for determining a medical indication for an order using the AI assisted medical indication selection support system of FIG. 1 in accordance with some embodiments of the inventive concept.

FIGS. 3-9 are flowcharts that illustrate operations for determining a medical indication for an order using the AI assisted medical indication selection support system in accordance with some embodiments of the inventive concept. Referring now to FIG. 3, the data pre-processor 205 receives first information associated with a patient, second information associated with a provider, and third information associated with an order. (Block 300). The neural network 210 determines one or more medical indications corresponding to the order responsive to receiving the first information, the second information, and the third information (Block 305).

Figure 4:
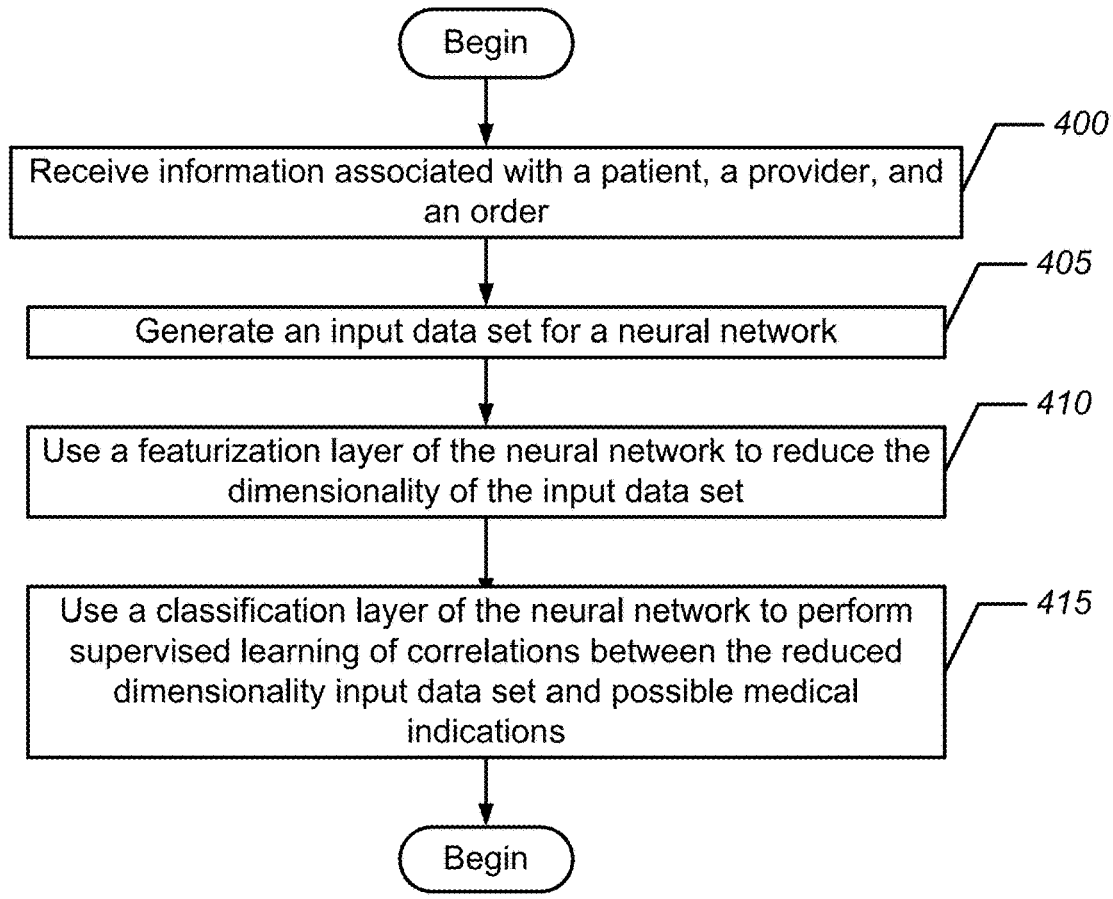

Referring now to FIG. 4, further operations of the neural network 210, according to some embodiments of the inventive concept, will now be described. As described above, the data pre-processor 205 receives first information associated with a patient, second information associated with a provider, and third information associated with an order. (Block 400). The data pre-processor 205 generates an input data set for the neural network 210 based on the first information, the second information, and the third information (Block 405). A featurization layer 220, 225 of the neural network 210 is used to automatically perform feature extraction on the input data set to reduce the dimensionality thereof (Block 410). A classification layer 230 of the neural network 210 is used to perform supervised learning of correlations between the input data set and a plurality of possible medical indications based on the feature extraction performed on the input data set (Block 415).

Figure 5:
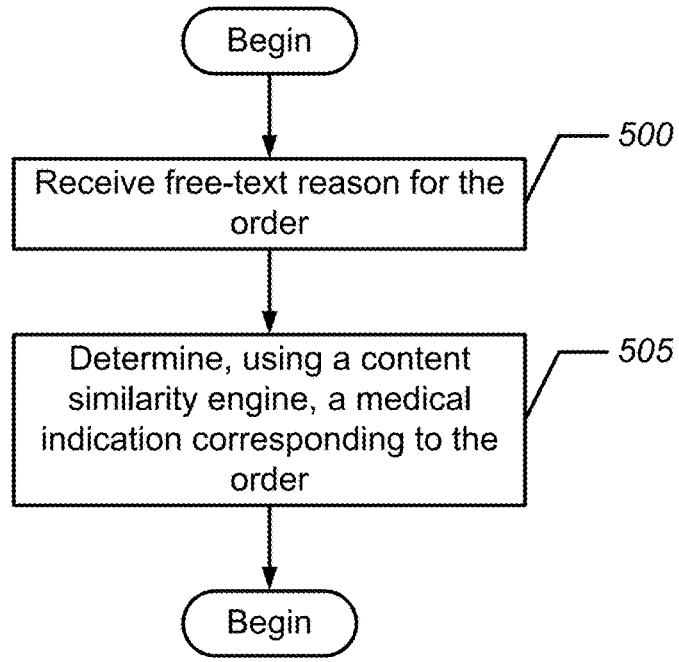

Referring to FIG. 5, operations of the content similarity engine 215 and natural language processor 240, according to some embodiments of the inventive concept, will now be described. The data pre-processor 205 receives a free-text reason for an order (Block 500). The content similarity engine 215 and natural language processor 240 determine one or more medical indications corresponding to the order responsive to receipt of the free-text reason (Block 505).

Figure 6:
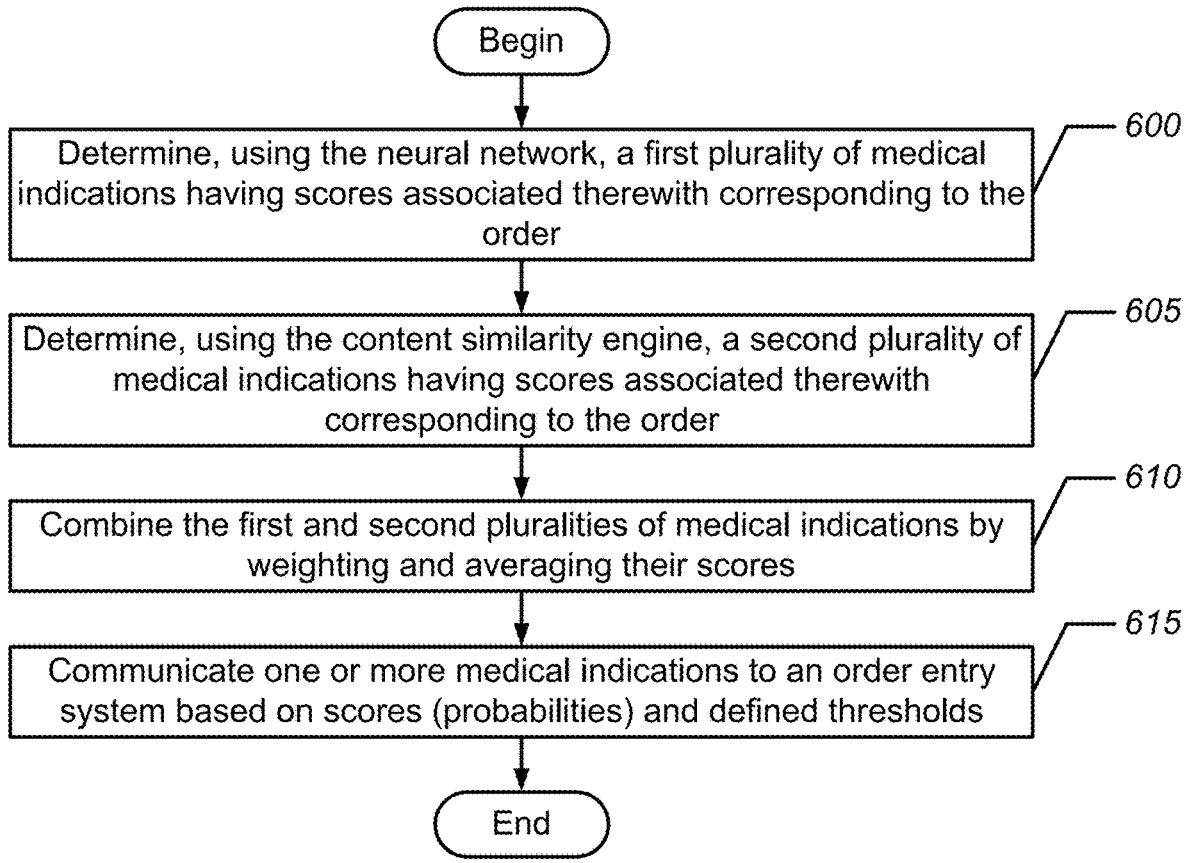

Referring now to FIG. 6, operations for combining the outputs of the neural network 210 and the content similarity engine 215, according to some embodiments of the inventive concept, will now be described. The neural network 210 determines a first plurality of indications having scores associated therewith that correspond to the order based on the patient, provider, and order information (Block 600). The content similarity engine 215 may process a free-text reason to determine a second plurality of medical indications having scores associated therewith that correspond to the order (Block 605). The combiner 220 may combine the first and second plurality of indications computing weighted averages of the scores for each of the medical indications output from the neural network 210 and the content similarity engine 215 (Block 610). One or more medical indications may be communicated to the health care facility server 105 and order entry system/EMR system 120 based on their scores (i.e., probabilities of being applicable to the order) and their scores' relationships to one or more defined thresholds as described above (Block 615).

Figure 7:
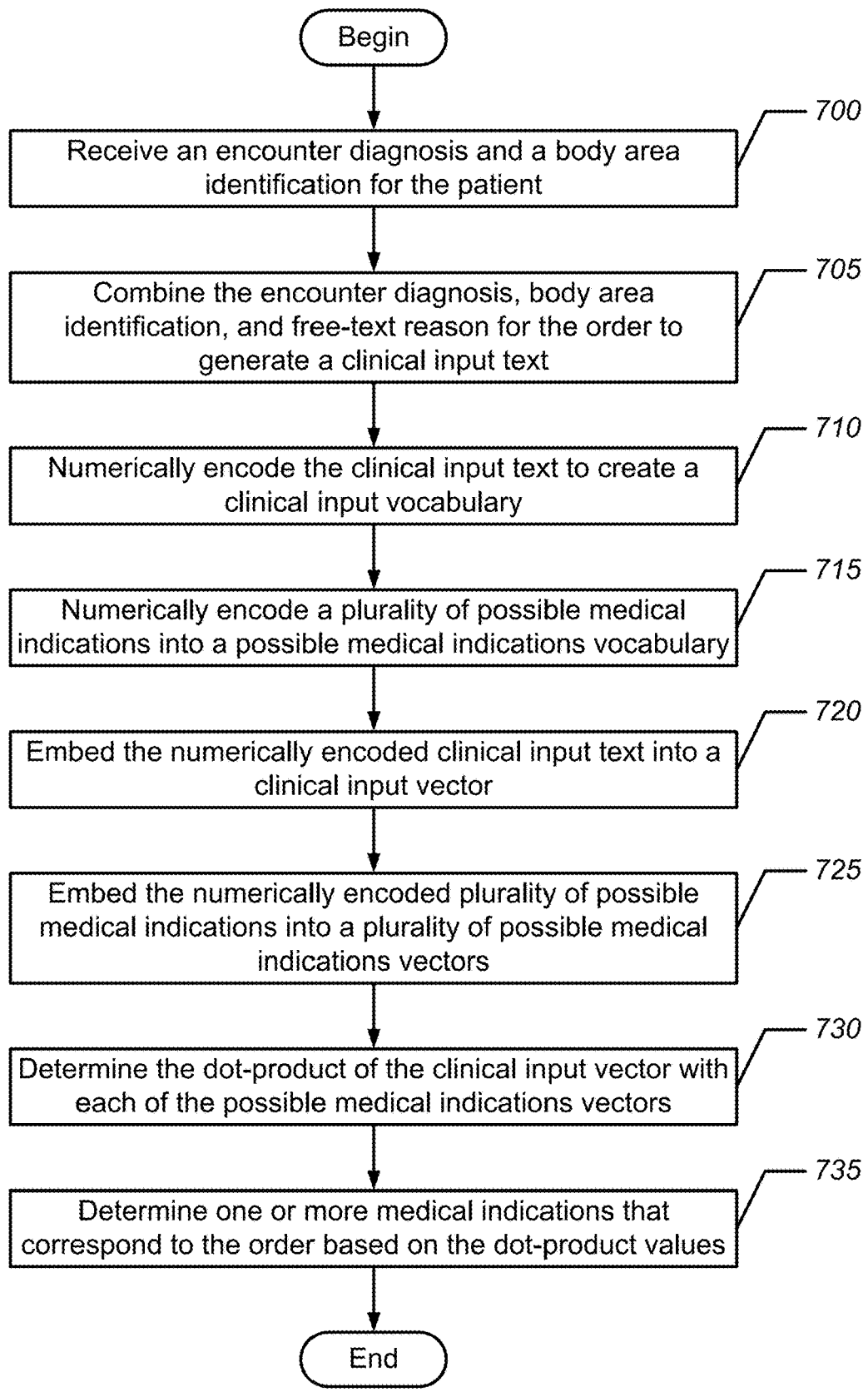

Referring now to FIG. 7, operations of the content similarity engine 215 and natural language processor 240, according to some embodiments of the inventive concept, will now be described. The data pre-processor 205 receives an encounter diagnosis and a body area identification of an order. (Block 700). The patient's encounter diagnosis along with the body area identification may be combined with the free-text reason to generate a clinical input text that captures the clinical aspects of the reason for the exam. (Block 705). The natural language processor 240 may numerically encode the clinical input text into a first sequence of words to create a clinical input vocabulary. The first sequence of words may first weights associated therewith, respectively, that are each indicative of the importance of respective ones of the first sequence of words in the clinical input vocabulary (Block 710). The natural language processor 240 may also numerically encode a plurality of possible medical indications into a second sequence of words to create a possible medical indications vocabulary. In some embodiments, the possible medical indications may be modified by repeating the first phrase in the clinical indication names to put more emphasis on the primary description of the respective medical indications. The second sequence of words may have second weights associated therewith, respectively, that are each indicative of the importance of respective ones of the second sequence of words in the possible medical indications vocabulary (Block 715). The natural language processor 240 embeds the numerically encoded clinical input text into a clinical input vector (Block 720) and also embeds the numerically encoded plurality of possible medical indications into a plurality of possible medical indications vectors (Block 725). The natural language processor 240 may then determine the dot-product values of the clinical input vector with each of the plurality of possible medical indications vectors (Block 730). These dot-product values may correspond to scores for each of the possible medical indications that are indicative of their respective probabilities of being applicable to the order. Thus, one or more medical indications may be selected from the list of possible medical indications as being applicable to the order based on their dot-product values/scores (Block 735).

Figure 8:
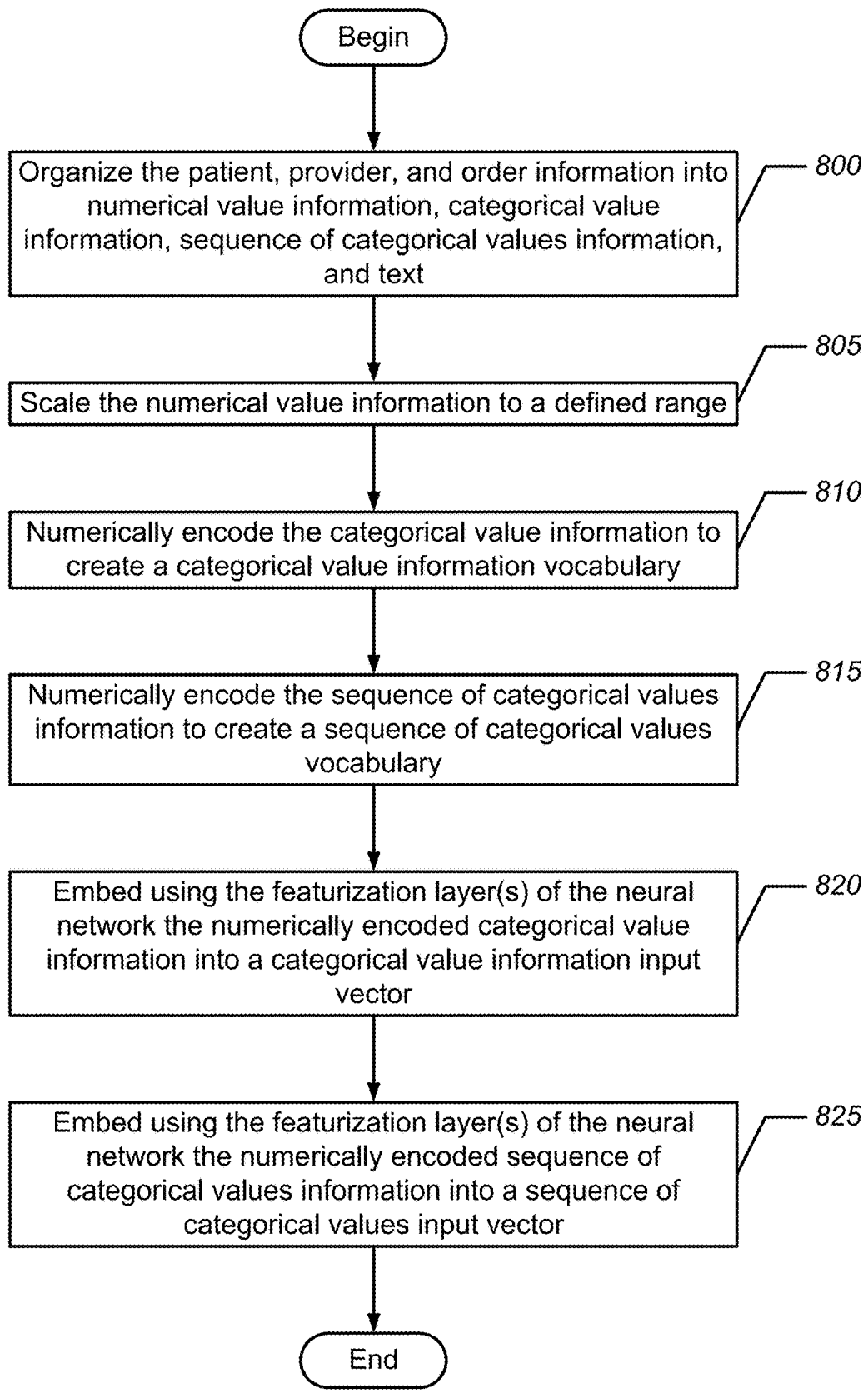

Referring now to FIG. 8, operations of the first featurization layer 220 of the neural network 210, according to some embodiments of the inventive concept, will now be described. As described above, the data pre-processor 205 may organize the patient, provider, and order information into numerical value information, categorical value information, and sequence of categorical values information (Block 800). The data pre-processor 205 may also scale the numerical value information to a defined range to generate scaled numerical value information (Block 805). The first featurization layer 220 numerically encodes the categorical value information to create a categorical value information vocabulary (Block 810) and numerically encodes the sequence of categorical values information to create a sequence of categorical values vocabulary (Block 815). The first featurization layer 220 may then embed the numerically encoded categorical value information into a categorical value information input vector (Block 820) and embed the numerically encoded sequence of categorical values information into a sequence of categorical values information input vector (Block 825).

Figure 9:
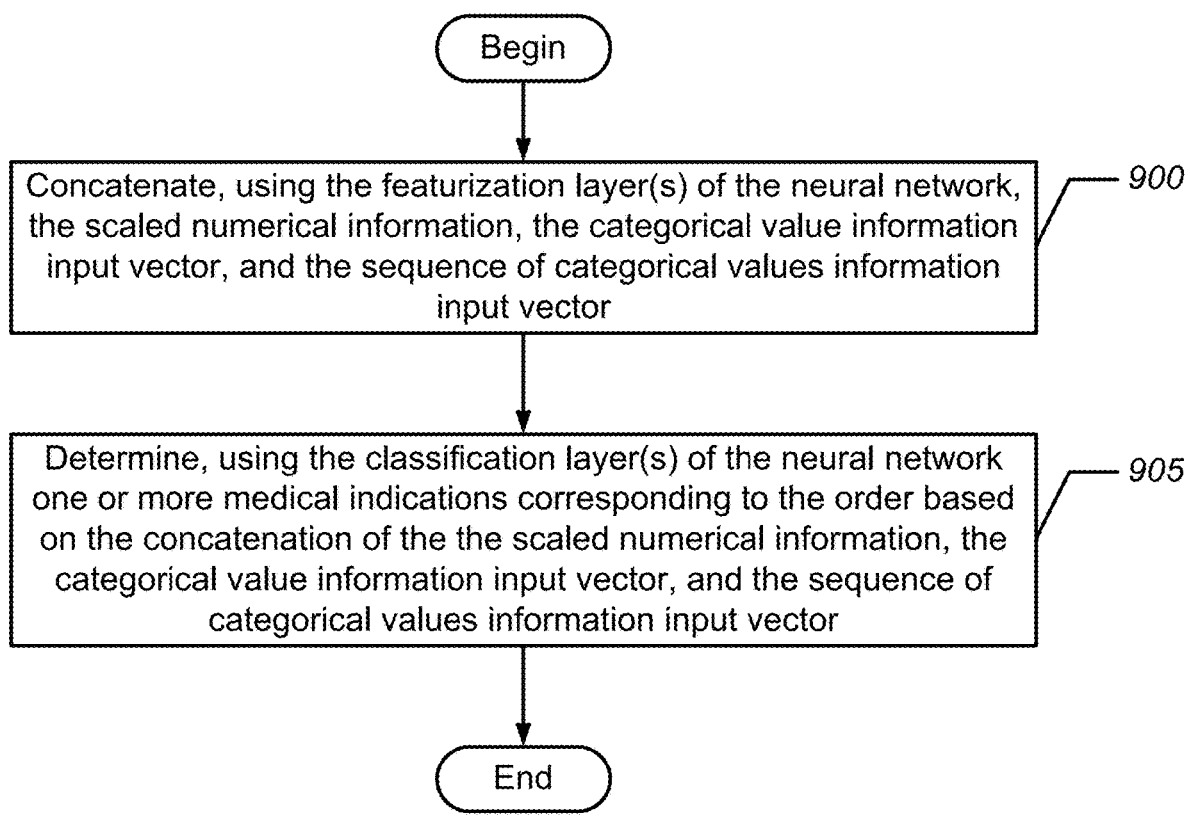

Referring now to FIG. 9, operations of the second featurization layer 225 and the classification layer(s) 230 of the neural network 210, according to some embodiments of the inventive concept, will now be described. The second featurization layer 225 may be configured to receive the scaled numerical information from the data pre-processor 205, the categorical value information input vector from the first featurization layer 220, and the sequence of categorical values information input vector from the first featurization layer 220 and to concatenate the scaled numerical information with the two input vectors (Block 900). The classification layer(s) 230 may be configured to determine one or more medical indications corresponding to the order responsive to the concatenation of the scaled numerical value information, the categorical value information input vector, and the sequence of categorical values information input vector.

Figure 10:
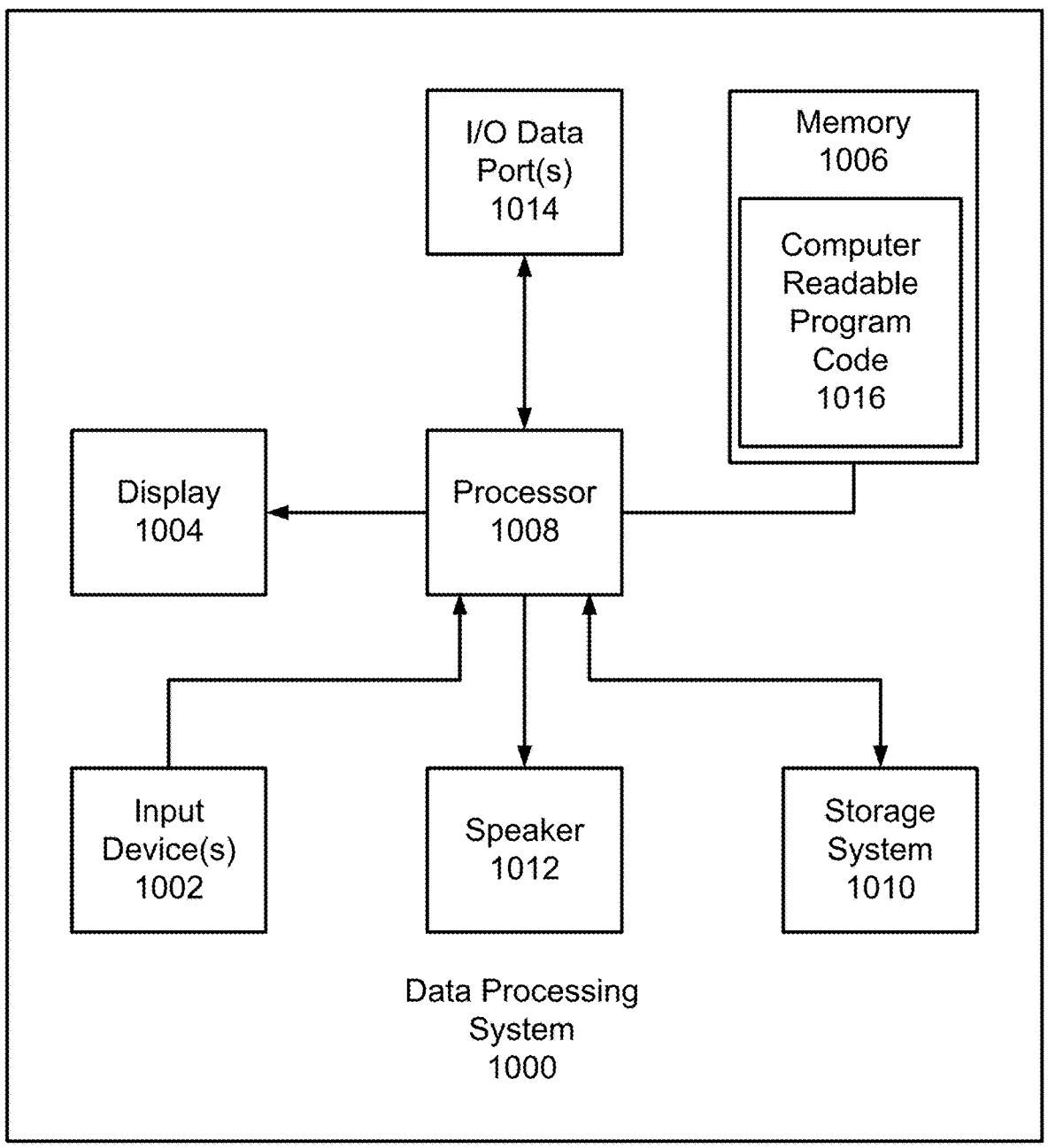
FIG. 10 is a data processing system that may be used to implement one or more servers in the AI assisted medical indication selection support system of FIG. 1 in accordance with some embodiments of the inventive concept.

Referring now to FIG. 10, a data processing system 1000 that may be used to implement the AI server 140 of FIG. 1, in accordance with some embodiments of the inventive concept, comprises input device(s) 1002, such as a keyboard or keypad, a display 1004, and a memory 1006 that communicate with a processor 1008. The data processing system 1000 may further include a storage system 1010, a speaker 1012, and an input/output (I/O) data port(s) 1014 that also communicate with the processor 1008. The processor 1008 may be, for example, a commercially available or custom microprocessor. The storage system 1010 may include removable and/or fixed media, such as floppy disks, ZIP drives, hard disks, or the like, as well as virtual storage, such as a RAMDISK. The I/O data port(s) 1014 may be used to transfer information between the data processing system 1000 and another computer system or a network (e.g., the Internet). These components may be conventional components, such as those used in many conventional computing devices, and their functionality, with respect to conventional operations, is generally known to those skilled in the art. The memory 1006 may be configured with computer readable program code 1016 to facilitate AI assisted medical indication selection according to some embodiments of the inventive concept.

Figure 11:
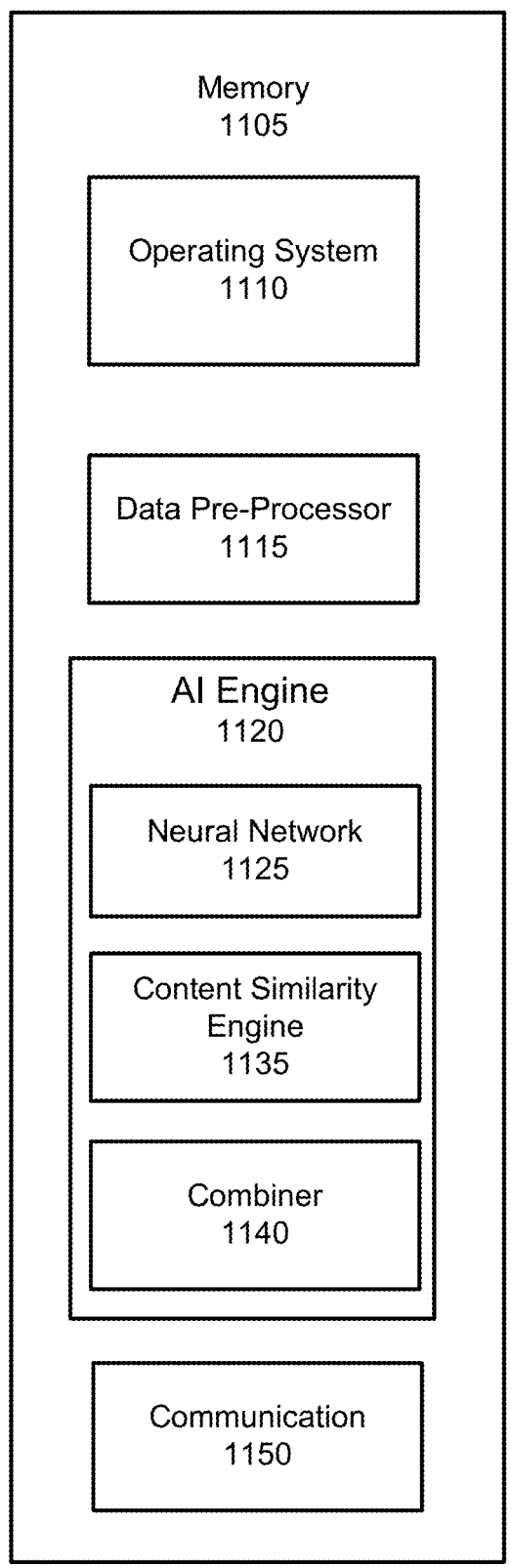
FIG. 11 is a block diagram that illustrates a software/hardware architecture for use in the AI assisted medical indication selection support system of FIG. 1 in accordance with some embodiments of the inventive concept.

FIG. 11 illustrates a memory 1105 that may be used in embodiments of data processing systems, such as the AI server 140 of FIG. 1 and the data processing system 1000 of FIG. 10, respectively, to facilitate AI assisted medical indication selection according to some embodiments of the inventive concept. The memory 1105 is representative of the one or more memory devices containing the software and data used for facilitating operations of the AI server 140 and AI engine 145 as described herein. The memory 1105 may include, but is not limited to, the following types of devices: cache, ROM, PROM, EPROM, EEPROM, flash, SRAM, and DRAM. As shown in FIG. 11, the memory 1105 may contain three or more categories of software and/or data: an operating system 1110, a data pre-processor module 1110, and an AI engine module 1120. In particular, the operating system 1110 may manage the data processing system's software and/or hardware resources and may coordinate execution of programs by the processor. The data pre-processor module 1115 may be configured to perform one or more of the operations described above with respect to the data pre-processor 205, block 300 of FIG. 3, blocks 400 and 405 of FIG. 4, block 500 of FIG. 5, blocks 700 and 705 of FIG. 7, and blocks 800 and 805 of FIG. 8. The AI engine module 1120 may comprise a neural network module 1125, a content similarity engine module 1135, and a combiner module 1140. The neural network module 1125 may be configured to perform one or more operations described above with respect to the neural network 210, including the first featurization layer 220, the second featurization layer 225, the classification layer(s) 230, and the output layer 235, block 305 of FIG. 3, blocks 410 and 415 of FIG. 4, blocks 600 and 605 of FIG. 6, blocks 810, 815, 820, and 825 of FIG. 8, and blocks 900 and 905 of FIG. 9. The content similarity engine module 1135 may be configured to perform one or more operations described above with respect to the content similarity engine 215, including the natural language processor 240, block 505 of FIG. 5, block 605 of FIG. 6, and blocks 710, 715, 720, 725, 730, and 735 of FIG. 7. The combiner module 1140 may be configured to perform one or more operations described above with respect to the combiner 220 and block 610 of FIG. 6. The communication module 1150 may be configured to perform one or more operations described above with respect to the medical indication(s) 245 of FIG. 2 and block 615 of FIG. 6.

Although FIGS. 10-11 illustrate hardware/software architectures that may be used in data processing systems, such as the AI server 140 of FIG. 1 and the data processing system 1000 of FIG. 10, respectively, in accordance with some embodiments of the inventive concept, it will be understood that the present invention is not limited to such a configuration but is intended to encompass any configuration capable of carrying out operations described herein.

Computer program code for carrying out operations of data processing systems discussed above with respect to FIGS. 1-11 may be written in a high-level programming language, such as Python, Java, C, and/or C++, for development convenience. In addition, computer program code for carrying out operations of the present invention may also be written in other programming languages, such as, but not limited to, interpreted languages. Some modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller.

Moreover, the functionality of the AI server 140 of FIG. 1 and the data processing system 1000 of FIG. 10 may each be implemented as a single processor system, a multi-processor system, a multi-core processor system, or even a network of stand-alone computer systems, in accordance with various embodiments of the inventive concept. Each of these processor/computer systems may be referred to as a "processor" or "data processing system."

The data processing apparatus described herein with respect to FIGS. 1-11 may be used to facilitate AI assisted medical indication selection according to some embodiments of the inventive concept described herein. These apparatus may be embodied as one or more enterprise, application, personal, pervasive and/or embedded computer systems and/or apparatus that are operable to receive, transmit, process and store data using any suitable combination of software, firmware and/or hardware and that may be standalone or interconnected by any public and/or private, real and/or virtual, wired and/or wireless network including all or a portion of the global communication network known as the Internet, and may include various types of tangible, non-transitory computer readable media. In particular, the memory 1105 when coupled to a processor includes computer readable program code that, when executed by the processor, causes the processor to perform operations including one or more of the operations described herein with respect to FIGS. 1-9.

Some embodiments of the inventive concept may provide an AI service that uses relevant data about the patient, provider, and/or order context to predict the most likely medical indications that would be relevant for the patient, provider, and/or order scenario. This may simplify and improve a provider's workflow in a health care facility and may improve the quality of care and patient outcomes in one or more of the following ways: predicting or recommending medical indications for an order with high specificity; ensuring regulatory compliance/appropriateness of an order by using a clinical decision support system in choosing a medical indication; identifying the most appropriate order with relatively high probability for a patient and/or reducing or eliminating unnecessary orders/tests for a patient; and making a provider's workflow more efficient and less time consuming as reviewing hundreds or thousands of possible medical indications can be avoided with the AI assisted medical indication selection support system reducing the number of medical indications to review to a manageable number or even automatically selecting the most likely medical indication when the probability of that medical indication being appropriate to the order exceeds a threshold.

FURTHER DEFINITIONS AND EMBODIMENTS

In the above description of various embodiments of the present inventive concept, it is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

The flowchart and block diagrams in the figures illustrate the architecture, functionality, and operation of possible implementations of systems, methods, and computer program products according to various aspects of the present inventive concept. In this regard, each block in the flowchart or block diagrams may represent a module, segment, or portion of code, which comprises one or more executable instructions for implementing the specified logical function (s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular aspects only and is not intended to be limiting of the inventive concept. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Like reference numbers signify like elements throughout the description of the figures.

In the above-description of various embodiments of the present inventive concept, aspects of the present inventive concept may be illustrated and described herein in any of a number of patentable classes or contexts including any new and useful process, machine, manufacture, or composition of matter, or any new and useful improvement thereof. Accordingly, aspects of the present inventive concept may be implemented entirely hardware, entirely software (including firmware, resident software, micro-code, etc.) or combining software and hardware implementation that may all generally be referred to herein as a "circuit," "module," "component," or "system." Furthermore, aspects of the present inventive concept may take the form of a computer program product comprising one or more computer readable media having computer readable program code embodied thereon.

Any combination of one or more computer readable media may be used. The computer readable media may be a computer readable signal medium or a computer readable storage medium. A computer readable storage medium may be, for example, but not limited to, an electronic, magnetic, optical, electromagnetic, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), an appropriate optical fiber with a repeater, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

The description of the present inventive concept has been presented for purposes of illustration and description, but is not intended to be exhaustive or limited to the inventive concept in the form disclosed. Many modifications and variations will be apparent to those of ordinary skill in the art without departing from the scope and spirit of the inventive concept. The aspects of the inventive concept herein were chosen and described to best explain the principles of the inventive concept and the practical application, and to enable others of ordinary skill in the art to understand the inventive concept with various modifications as are suited to the particular use contemplated.

What is claimed is:

1. A computer-implemented method, comprising:
   receiving, by one or more processors, first information associated with a patient, second information associated with a provider, and third information associated with an order issued by the provider;
   performing, by the one or more processors and using one or more layers of an artificial intelligence engine that comprises a multi-layer neural network, feature extraction on the first information, the second information, and the third information to reduce a dimensionality thereof;
   determining, by the one or more processors and using the artificial intelligence engine that is trained using a data set that includes information on evidence based guidelines that support medical indication selection, a probability that a medical indication corresponds to the order based on the feature extraction from the first information, the second information, and the third information having the reduced dimensionality; and
   automatically communicating, by the one or more processors and to an order entry system for entry therein, without input from the provider, an automatic selection of the medical indication when the probability exceeds a threshold.

2. The computer-implemented method of claim 1, wherein the artificial intelligence engine further comprises a content similarity engine; and
   wherein the medical indication is a first medical indication, the method further comprising:
   receiving, by the one or more processors, a free-text reason for the order; and
   determining, by the one or more processors and using the content similarity engine, a second medical indication corresponding to the order responsive to receiving the free-text reason.

3. The computer-implemented method of claim 2, wherein determining, using the artificial intelligence engine, the first medical indication comprises:
   determining, using the multi-layer neural network, a first plurality of medical indications corresponding to the order responsive to the first information, the second information, and the third information; and
   wherein determining, using the content similarity engine, the second medical indication comprises:
   determining using the content similarity engine, a second plurality of medical indications responsive to the free-text reason;
   wherein the first plurality of medical indications have a first plurality of scores associated therewith, respectively; and
   wherein the second plurality of medical indications have a second plurality of scores associated therewith, respectively;
   wherein the method further comprises:
   generating, by the one or more processors, a third plurality of medical indications, the third plurality of medical indications comprising a combination of the first plurality of medical indications and the second plurality of medical indications, each of the third plurality of medical indications having a respective one of the first plurality of scores associated therewith and a respective one of the second plurality of scores associated therewith, such that the respective one of the first plurality of scores is zero when the respective one of the third plurality of medical indications is not in the first plurality of medical indications and the respective one of the second plurality of scores is zero when the respective one of the third plurality of medical indications is not in the second plurality of medical indications; and
   generating, by the one or more processors, a third plurality of scores associated with the third plurality of medical indications, respectively;
   wherein the third plurality of scores comprises a plurality of weighted averages of the first plurality of scores associated with the third plurality of medical indications and the second plurality of scores associated with the third plurality of medical indications, respectively.

4. The computer-implemented method of claim 3, wherein the third plurality of scores corresponds to probabilities of the third plurality of medical indications being applicable to the order, respectively; and
   wherein the method further comprises:
   communicating, by the one or more processors, to the order entry system for entry therein, without input from the provider, an automatic selection of one of the third plurality of medical indications having a highest one of the probabilities associated therewith when the highest one of the probabilities exceeds the threshold.

5. The computer-implemented method of claim 4, further comprising:
   communicating, by the one or more processors, to the order entry system N of the third plurality of medical indications having N highest probabilities associated therewith, respectively, when the highest one of the probabilities does not exceed the threshold;
   wherein N is less than a total number of the plurality of third medical indications.

6. The computer-implemented method of claim 4, wherein the threshold is a first threshold, the method further comprising:
   communicating, by the one or more processors, to the order entry system an indication that none of the third plurality of medical indications is applicable to the order when a highest one of the probabilities is less than a second threshold.

7. The computer-implemented method of claim 2, further comprising:
   receiving, by the one or more processors, an encounter diagnosis for the patient and a body area identification based on the order;

combining, by the one or more processors, the encounter diagnosis for the patient, the body area identification based on the order, and the free-text reason for the order to generate a clinical input text;

numerically encoding, by the one or more processors, the clinical input text into a first sequence of words to create a clinical input vocabulary, the first sequence of words having first weights associated therewith, respectively, that are each indicative of an importance of respective ones of the first sequence of words in the clinical input vocabulary;

numerically encoding, by the one or more processors, a plurality of possible medical indications into a second sequence of words to create a possible medical indications vocabulary, the second sequence of words having second weights associated therewith, respectively, that are each indicative of the importance of respective ones of the second sequence of words in the possible medical indications vocabulary;

embedding, by the one or more processors, the numerically encoded clinical input text into a clinical input vector;

embedding, by the one or more processors, the numerically encoded plurality of possible medical indications into a plurality of possible medical indications vectors; and determining, by the one or more processors, a dot-product of the clinical input vector with each of the plurality of possible medical indications vectors;

wherein determining, using the content similarity engine, the second medical indication responsive to receiving the free-text reason comprises:

determining, by the one or more processors, the second medical indication based on the dot-product of the clinical input vector with each of the plurality of possible medical indications vectors.

8. The computer-implemented method of claim 7, further comprising:

duplicating, by the one or more processors, a first phrase in each of the plurality of possible medical indications before numerically encoding the plurality of possible medical indications into the second sequence.

9. The computer-implemented method of claim 2, wherein the first information associated with the patient comprises at least one of an age, a gender, a problem list, an encounter diagnosis, a patient class, or a medical center department;

wherein the second information associated with the provider comprises at least one of a provider identifier or a provider specialty; and wherein the third information associated with the order comprises at least one of an order name, order identification, order modality, order contrast, or body area identification.

10. The computer-implemented method of claim 9, further comprising:

organizing, by the one or more processors, the first, second, and third information into numeric value information, categorical value information, and sequence of categorical values information;

scaling, by the one or more processors, the numerical value information to a defined range to generate scaled numerical value information;

numerically encoding, by the one or more processors, the categorical value information to create a categorical value information vocabulary;

numerically encoding, by the one or more processors, the sequence of categorical values information to create a sequence of categorical values vocabulary;

embedding, by the one or more processors and using a first layer of the neural network, the numerically encoded categorical value information into a categorical value information input vector; and embedding, by the one or more processors and using the first layer of the neural network, the numerically encoded sequence of categorical values information into a sequence of categorical values information input vector.

11. The computer-implemented method of claim 10, further comprising:

concatenating, by the one or more processors and using a second layer of the neural network, the scaled numerical value information, the categorical value information input vector, and the sequence of categorical values information input vector;

wherein determining, using a multi-layer neural network, the medical indication comprises:

determining, by the one or more processors and using a third layer of the neural network, the medical indication corresponding to the order responsive to a concatenation of the scaled numerical value information, the categorical value information input vector, and the sequence of categorical values information input vector.

12. The computer-implemented method of claim 11, wherein performing feature extraction on the first information, the second information and the third information comprises:

performing, by the one or more processors and the first and second layers of the multi-layer neural network, feature extraction on the numeric value information, the categorical value information, the sequence of categorical values information, or text information to reduce the dimensionality thereof.

13. The computer-implemented method of claim 12, wherein the third layer of the multi-layer neural network is a classification layer that is configured to perform supervised learning of correlations between the scaled numerical value information, the categorical value information input vector, the sequence of categorical values information input vector, and a text information input vector and a plurality of possible medical indications based on the feature extraction performed by the second layer of the multi-layer neural network.

14. A system, comprising:

one or more processors; and at least one memory coupled to the one or more processors and comprising computer readable program code embodied in the at least one memory that is executable by the one or more processors to perform operations comprising:

receiving, by the one or more processors, first information associated with a patient, second information associated with a provider, and third information associated with an order issued by the provider;

performing, by the one or more processors and using one or more layers of an artificial intelligence engine that comprises a multi-layer neural network, feature extraction on the first information, the second information, and the third information to reduce a dimensionality thereof;

determining, by the one or more processors and using the artificial intelligence engine that is trained using a data set that includes information on evidence based guidelines that support medical indication selection, a probability that a medical indication corresponds to the order based on the feature extraction from the first information, the second information, and the third information having the reduced dimensionality; and automatically communicating, by the one or more processors and to an order entry system for entry therein, without input from the provider, an automatic selection of the medical indication when the probability exceeds a threshold.

15. The system of claim 14, wherein the artificial intelligence engine further comprises a content similarity engine; and wherein the medical indication is a first medical indication, the operations further comprising:

receiving a free-text reason for the order; and determining, using the content similarity engine, a second medical indication corresponding to the order responsive to receiving the free-text reason.

16. The system of claim 15, wherein determining, using the artificial intelligence engine, the first medical indication comprises:

determining, using the multi-layer neural network, a first plurality of medical indications corresponding to the order responsive to the first information, the second information, and the third information; and wherein determining, using the content similarity engine, the second medical indication comprises:

determining using the content similarity engine, a second plurality of medical indications responsive to the free-text reason;

wherein the first plurality of medical indications have a first plurality of scores associated therewith, respectively; and wherein the second plurality of medical indications have a second plurality of scores associated therewith, respectively;

wherein the operations further comprise:

generating a third plurality of medical indications, the third plurality of medical indications comprising a combination of the first plurality of medical indications and the second plurality of medical indications, each of the third plurality of medical indications having a respective one of the first plurality of scores associated therewith and a respective one of the second plurality of scores associated therewith, such that the respective one of the first plurality of scores is zero when the respective one of the third plurality of medical indications is not in the first plurality of medical indications and the respective one of the second plurality of scores is zero when the respective one of the third plurality of medical indications is not in the second plurality of medical indications; and generating a third plurality of scores associated with the third plurality of medical indications, respectively;

wherein the third plurality of scores comprises a plurality of weighted averages of the first plurality of scores associated with the third plurality of medical indications and the second plurality of scores associated with the third plurality of medical indications, respectively.

17. The system of claim 15, wherein the operations further comprise:

receiving an encounter diagnosis for the patient and a body area identification based on the order;

combining the encounter diagnosis for the patient, the body area identification based on the order, and the free-text reason for the order to generate a clinical input text;

numerically encoding the clinical input text into a first sequence of words to create a clinical input vocabulary, the first sequence of words having first weights associated therewith, respectively, that are each indicative of an importance of respective ones of the first sequence of words in the clinical input vocabulary;

numerically encoding a plurality of possible medical indications into a second sequence of words to create a possible medical indications vocabulary, the second sequence of words having second weights associated therewith, respectively, that are each indicative of the importance of respective ones of the second sequence of words in the possible medical indications vocabulary;

embedding the numerically encoded clinical input text into a clinical input vector;

embedding the numerically encoded plurality of possible medical indications into a plurality of possible medical indications vectors; and determining a dot-product of the clinical input vector with each of the plurality of possible medical indications vectors;

wherein determining, using the content similarity engine, the second medical indication responsive to receiving the free-text reason comprises:

determining the second medical indication based on the dot-product of the clinical input vector with each of the plurality of possible medical indications vectors.

18. One or more non-transitory computer readable storage media comprising computer readable program code embodied in the media that is executable by one or more processors to perform operations comprising:

receiving, by the one or more processors, first information associated with a patient, second information associated with a provider, and third information associated with an order issued by the provider;

performing, by the one or more processors and using one or more layers of an artificial intelligence engine that comprises a multi-layer neural network, feature extraction on the first information, the second information, and the third information to reduce a dimensionality thereof;

determining, by the one or more processors and using the artificial intelligence engine that is trained using a data set that includes information on evidence based guidelines that support medical indication selection, a probability that a medical indication corresponds to the order based on the feature extraction from the first information, the second information, and the third information having the reduced dimensionality; and automatically communicating, by the one or more processors and to an order entry system for entry therein, without input from the provider, an automatic selection of the medical indication when the probability exceeds a threshold.

19. The one or more non-transitory computer readable storage media of claim 18, wherein the artificial intelligence engine further comprises a content similarity engine; and wherein the medical indication is a first medical indication, the operations further comprising:

receiving a free-text reason for the order; and determining, using the content similarity engine, a second medical indication corresponding to the order responsive to receiving the free-text reason.

20. The one or more non-transitory computer readable storage media of claim 19, wherein determining, using the artificial intelligence engine, the first medical indication comprises:
   determining, using the multi-layer neural network, a first plurality of medical indications corresponding to the order responsive to the first information, the second information, and the third information; and
   wherein determining, using the content similarity engine, the second medical indication comprises:
   determining using the content similarity engine, a second plurality of medical indications responsive to the free-text reason;
   wherein the first plurality of medical indications have a first plurality of scores associated therewith, respectively; and
   wherein the second plurality of medical indications have a second plurality of scores associated therewith, respectively;
   wherein the operations further comprise:
   generating a third plurality of medical indications, the third plurality of medical indications comprising a combination of the first plurality of medical indications and the second plurality of medical indications, each of the third plurality of medical indications having a respective one of the first plurality of scores associated therewith and a respective one of the second plurality of scores associated therewith, such that the respective one of the first plurality of scores is zero when the respective one of the third plurality of medical indications is not in the first plurality of medical indications and the respective one of the second plurality of scores is zero when the respective one of the third plurality of medical indications is not in the second plurality of medical indications; and
   generating a third plurality of scores associated with the third plurality of medical indications, respectively;
   wherein the third plurality of scores comprises a plurality of weighted averages of the first plurality of scores associated with the third plurality of medical indications and the second plurality of scores associated with the third plurality of medical indications, respectively.

* * * * *

UNITED STATES PATENT AND TRADEMARK OFFICE
CERTIFICATE OF CORRECTION

| | | |
|---|---|---|
| PATENT NO. | : 12,148,513 B2 | Page 1 of 1 |
| APPLICATION NO. | : 16/836575 | |
| DATED | : November 19, 2024 | |
| INVENTOR(S) | : Henrik Johansson et al. | |

It is certified that error appears in the above-identified patent and that said Letters Patent is hereby corrected as shown below:

On the Title Page

Item (57), Line 3, "order," should be -- order; --.

In the Drawings

At Fig. 9, Sheet 7 of 9, Tag "905", Line 1, "network" should be -- network, --.

At Fig. 9, Sheet 7 of 9, Tag "905", Line 3, "the the" should be -- the --.

In the Specification

At Column 16, Line 17, "data pre-processor module 1110," should be -- data pre-processor module 1115, --.

Signed and Sealed this
Twentieth Day of May, 2025

Coke Morgan Stewart
*Acting Director of the United States Patent and Trademark Office*